United States Patent
McCloskey et al.

(10) Patent No.: US 6,420,588 B1
(45) Date of Patent: Jul. 16, 2002

(54) INTERFACIAL METHOD OF PREPARING ESTER-SUBSTITUTED DIARYL CARBONATES

(75) Inventors: Patrick Joseph McCloskey, Watervliet; Timothy Brydon Burnell, Schenectady; Daniel Joseph Brunelle, Burnt Hills; Elliott West Shanklin, Altamont; Paul Michael Smigelski, Jr., Schenectady, all of NY (US); Ganesh Kailasam, Murcia (ES)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/911,440

(22) Filed: Jul. 24, 2001

(51) Int. Cl.$^7$ .............................................. C07C 69/96
(52) U.S. Cl. ...................................................... 558/274
(58) Field of Search ......................................... 558/274

(56) References Cited

U.S. PATENT DOCUMENTS

| | | | |
|---|---|---|---|
| 5,874,605 A | * 2/1999 | Yoshida et al. | 558/274 |
| 5,900,501 A | * 5/1999 | Ooms et al. | 558/274 |
| 5,980,445 A | * 11/1999 | Mizukami et al. | 58/274 |
| 6,093,842 A | * 7/2000 | Oyevaar et al. | 558/274 |
| 6,262,210 B1 | * 7/2001 | Tojo et al. | 526/270 |
| 6,294,684 B1 | * 9/2001 | de Bruin et al. | 558/274 |
| 6,348,613 B2 | * 2/2002 | Miyamoto et al. | 558/274 |
| 6,350,893 B1 | * 2/2002 | Ritzer et al. | 558/275 |

FOREIGN PATENT DOCUMENTS

| EP | 980861 A1 | 2/2000 |
|---|---|---|
| JP | 11302228 | 11/1999 |
| WO | 9845246 | 10/1998 |

\* cited by examiner

*Primary Examiner*—Deborah C. Lambkin
(74) *Attorney, Agent, or Firm*—Andrew J. Caruso; Noreen C. Johnson

(57) ABSTRACT

High yields of ester-substituted diary carbonates such as bis-methyl salicyl carbonate were obtained by the condensation of methyl salicylate with phosgene in the presence of a phase transfer catalyst (PTC) in an interfacial reaction system in which the pH of the aqueous phase was greater than 9.3. Using the method of the present invention conversions of greater than 99% were obtained whereas under standard conditions using triethylamine as the catalyst conversions were limited to 70–75% of the methyl salicylate starting material even with a 20 mole % excess of added phosgene. The optimized conditions of the of the present invention use only a slight excess of phosgene and represent an attractive route for the manufacture of bis methyl salicyl carbonate and ester-substituted diaryl carbonates generally.

22 Claims, No Drawings

INTERFACIAL METHOD OF PREPARING ESTER-SUBSTITUTED DIARYL CARBONATES

BACKGROUND OF THE INVENTION

This invention relates to a method of making ester-substituted diaryl carbonates and in particular to a method of making bis methyl salicyl carbonate.

Ester-substituted diaryl carbonates such as bis-methyl salicyl carbonate have proven to be useful starting materials in the preparation of polycarbonates via the melt reaction of a diaryl carbonate with aromatic dihydroxy compounds. See for example, U.S. Pat. No. 4,323,668 in which rates of polymerization of bis-methyl salicyl carbonate with bisphenol A were shown to be higher than the corresponding rates of polymerization of bisphenol A with an unsubstituted diaryl carbonate, diphenyl carbonate. Notwithstanding the simplicity of its structure there are few reported preparations of ester-substituted diaryl carbonates.

A classical preparation of diaryl carbonates involves the reaction of a hydroxy aromatic compound such as phenol with phosgene gas in a two phase reaction system comprising water, an acid acceptor such as sodium hydroxide and a solvent such as methylene chloride or chloroform. Typical interfacial conditions used to prepare diphenyl carbonate (DPC) utilize water and methylene chloride phases, sodium hydroxide as a pH control measure and triethylamine as a catalyst. Under such conditions it is possible to convert phenol to DPC in essentially quantitative yield. However, application of these same conditions to methyl salicylate results in only modest conversion of this ester-substituted phenol to the corresponding diaryl carbonate. Even the use of as much as 20 percent excess phosgene does not result in conversion of more than 70 to 75% of methyl salicylate to the bis methyl salicyl carbonate.

It would be desirable, therefore, to discover means for the efficient preparation of ester-substituted diaryl carbonates generally, and in particular it would be desirable to discover a highly efficient means of preparing bis-methyl salicyl carbonate from methyl salicylate and phosgene.

BRIEF SUMMARY OF THE INVENTION

The present invention relates to a method of preparing ester-substituted diaryl carbonates, said method having a contact time, said method comprising contacting an ester-substituted phenol with phosgene and a phase transfer catalyst in the presence of an organic solvent and an aqueous phase wherein the aqueous phase is maintained at a pH of at least about 9.3 throughout the contact time, said phosgene being used in an amount corresponding to between about 0.95 and about 1.20 molar equivalents based on said ester-substituted phenol. In one embodiment of the present invention, there is provided a means whereby at least 90% of the ester-substituted phenol is converted into product ester-substituted diaryl carbonate.

The present invention further relates to a high yield method of preparing bis-methyl salicyl carbonate, a valuable starting material for use in the melt polymerization of bisphenols to afford polycarbonates.

DETAILED DESCRIPTION OF THE INVENTION

The present invention may be understood more readily by reference to the following detailed description of preferred embodiments of the invention and the examples included therein. In the following specification and the claims which follow, reference will be made to a number of terms which shall be defined to have the following meanings:

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

As used herein the term "polycarbonate" refers to polycarbonates incorporating structural units derived from one or more dihydroxy aromatic compounds and includes copolycarbonates and polyester carbonates.

As used herein, the term "melt polycarbonate" refers to a polycarbonate made by a process comprising the transesterification of a diaryl carbonate with a bisphenol.

"Catalytically effective amount" refers to the amount of the catalyst at which catalytic performance is exhibited.

As used herein the term "contact time" is used interchangeably with reaction time.

As used herein the term "alkyl radical" refers to a radical having a valence of at least one comprising a linear or branched array of atoms which is not cyclic. The array may include heteroatoms such as nitrogen, sulfur and oxygen or may be composed exclusively of carbon and hydrogen. Examples of alkyl radicals include methyl, methylene, ethyl, ethylene, hexyl, hexamethylene and the like.

As used herein the term "aromatic radical" refers to a radical having a valence of at least one comprising at least one aromatic group. Examples of aromatic radicals include phenyl, pyridyl, furanyl, thienyl, naphthyl, phenylene, and biphenyl. The term includes groups containing both aromatic and aliphatic components, for example a benzyl group.

As used herein the term "cycloalkyl radical" refers to a radical having a valance of at least one comprising an array of atoms which is cyclic but which is not aromatic. The array may include heteroatoms such as nitrogen, sulfur and oxygen or may be composed exclusively of carbon and hydrogen. Examples of cycloalkyl radicals include cyclcopropyl, cyclopentyl cyclohexyl, tetrahydrofuranyl and the like.

In the present invention it has been discovered that ester-substituted phenols such as methyl salicylate are efficiently converted to ester-substituted diaryl carbonates such as bis-methyl salicyl carbonate under mild reaction conditions while minimizing the use of excess phosgene.

In one aspect the present invention provides a method for the efficient preparation of an ester-substituted diaryl carbonate having structure I

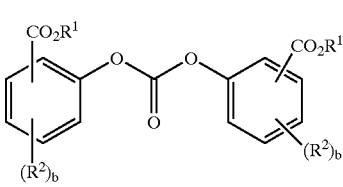

wherein $R^1$ is independently at each occurrence $C_1$–$C_{20}$ alkyl radical, $C_4$–$C_{20}$ cycloalkyl radical or $C_4$–$C_{20}$ aromatic radical, $R^2$ is independently at each occurrence a hydrogen atom, halogen atom, cyano group, nitro group, $C_1$–$C_{20}$ alkyl radical, $C_4$–$C_{20}$ cycloalkyl radical, $C_4$–$C_{20}$ aromatic radical, $C_1$–$C_{20}$ alkoxy radical, $C_4$–$C_{20}$ cycloalkoxy radical, $C_4$–$C_{20}$ aryloxy radical, $C_1$–$C_{20}$ alkylthio radical, $C_4$–$C_{20}$ cycloalkylthio radical, $C_4$–$C_{20}$ arylthio radical, $C_1$–$C_{20}$ alkylsulfinyl radical, $C_4$–$C_{20}$ cycloalkylsulfinyl radical, $C_4$–$C_{20}$ arylsulfinyl radical, $C_1$–$C_{20}$ alkylsulfonyl radical $C_4$–$C_{20}$ cycloalkylsulfonyl radical, $C_4$–$C_{20}$ arylsulfonyl radical, $C_1$–$C_{20}$ alkoxycarbonyl radical, $C_4$–$C_{20}$ cycloalkoxycarbonyl radical, $C_4$–$C_{20}$ aryloxycarbonyl radical, $C_2$–$C_{60}$ alkylamino radical, $C_6$–$C_{60}$ cycloalkylamino radical, $C_5$–$C_{60}$ arylamino radical, $C_1$–$C_{40}$ alkylaminocarbonyl radical, $C_4$–$C_{40}$ cycloalkylaminocarbonyl radical, $C_4$–$C_{40}$ arylaminocarbonyl radical, and $C_1$–$C_{20}$ acylamino radical; and b is independently at each occurrence an integer 0–4.

Examples of ester-substituted diaryl carbonates which may be prepared using the method of the present invention include bis-methyl salicyl carbonate (CAS Registry No. 82091-12-1), bis-ethyl salicyl carbonate, bis-propyl salicyl carbonate, bis-butyl salicyl carbonate, bis-benzyl salicyl carbonate, bis-methyl 4-chlorosalicyl carbonate and the like. Typically bis-methyl salicyl carbonate is preferred for use in melt polycarbonate synthesis due to its lower molecular weight and higher vapor pressure.

According to the method of the present invention an ester-substituted phenol is contacted with phosgene in an amount equivalent to from about 0.95 to about 1.20, preferably about 1.0 to about 1.1 and even more preferably about 1.01 to about 1.05 moles of phosgene per mole of ester-substituted phenol, said contact taking place in a in a two phase system comprising water and a water-immiscible solvent, an acid acceptor, a phase transfer catalyst, and optionally a tertiary amine catalyst, the ester-substituted phenol being contacted with said phosgene for a contact time of sufficient length to allow the conversion of at least 90% of the ester-substituted phenol into the product ester-substituted diaryl carbonate I.

The ester-substituted phenol is at least one compound selected from among phenols having structure II

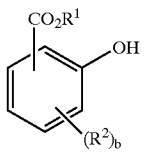

II wherein $R^1$ and $R^2$ are defined as in structure I and b is an integer 0–4.

Examples of ester-substituted phenols which may serve as starting materials for the method of the present invention include methyl salicylate, ethyl salicylate, propyl salicylate, butyl salicylate, benzyl salicylate, methyl 4-chlorosalicylate and the like. Typically, methyl salicylate is preferred.

The two phase system is comprised of an aqueous phase and an organic phase. The pH of the aqueous phase is controlled throughout the reaction by the addition of aqueous base. Suitable bases include alkali metal hydroxides such as sodium hydroxide and lithium hydroxide and alkaline earth metal hydroxides such as calcium hydroxide and magnesium hydroxide. An aqueous solution of sodium hydroxide containing from about 5 to about 50 percent by weight NaOH is preferred. Care must be taken in order to maintain a pH of the aqueous phase of at least about 9.3 during the contact time because rates of ester-substituted diaryl carbonate formation drop dramatically at lower pH. In one embodiment of the present invention the pH of the aqueous phase is maintained at between about 9.3 and about 12, preferably between about 10.3 and about 12.

The organic phase is at least one solvent said solvent being immiscible with water. The organic phase may comprise a halogenated or a non-halogenated solvent. Examples of halogenated solvents suitable for use in the method of the present invention are methylene chloride and chloroform. Examples of non-halogenated solvents suitable for use in the method of the present invention are toluene and ethyl acetate. The amount of solvent used is such that there is sufficient solvent to dissolve the ester-substituted phenol. Typically, a solution of the ester-substituted phenol in the water immiscible solvent contains between about 5 and about 50 weight percent ester-substituted phenol. In one embodiment of the present invention the volume of the aqueous phase is roughly equal to the volume of the organic phase at the outset of the reaction.

The contact between the ester-substituted phenol and phosgene may take place at below ambient temperature, ambient temperature or above ambient temperature. In one embodiment of the present invention ester-substituted phenol is contacted with phosgene at a temperature of between about 0° C. and about 50° C. preferably between about 10° C. and about 40° C.

The contact between the ester-substituted phenol and phosgene is of a sufficient length of time such that greater than 90% preferably greater than 95% and still more preferably greater than 98% of the starting ester-substituted phenol is converted to product ester-substituted diaryl carbonate and is referred to as the reaction time. In one embodiment the present invention the reaction time is in a range between about 5 and about 60 minutes. In embodiments of the present invention in which phosgene is added to a solution of the ester-substituted phenol reaction times are limited by the rate of phosgene addition.

The method of the present invention relies upon the unexpected finding that a phase transfer catalyst dramatically improves the conversion of ester-substituted phenols to product diaryl carbonates when said phenols are contacted with phosgene in a two phase reaction system comprising aqueous and organic phases in which the pH of the aqueous is controlled by the addition of an aqueous base such as aqueous sodium hydroxide. Suitable phase transfer catalysts are widely available and include quaternary ammonium salts of aliphatic amines, quaternary ammonium salts of aromatic amines, quaternary phosphonium salts, sulfonium salts, polyethers and the like. Quaternary ammonium salts of aliphatic amines are illustrated by methyl tributyl ammonium chloride, tetramethyl ammonium chloride and the like. Quaternary ammonium salts of aromatic amines are illustrated by N-benzyl pyridinium chloride, N-benzyl 4-N',N'-dimethylamino pyridinium chloride and the like. Quaternary ammonium salts include hexaalkyl guanidinium compounds such as hexaethyl guanidinium chloride. Quaternary phosphonium salts are illustrated by tetrabutyl phosphonium acetate and the like. Sulfonium salts are illustrated by trimethyl sulfonium chloride and the like. Polyethers are illustrated by polyethylene glycol and crown ethers such as 18-crown 6 and the like.

In one embodiment of the present invention the phase transfer catalyst is a quaternary ammonium compound having structure III

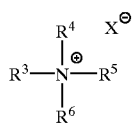

III wherein $R^3$–$R^6$ are independently a $C_1$–$C_{20}$ alkyl radical, $C_4$–$C_{20}$ cycloalkyl radical or a $C_4$–$C_{20}$ aryl radical and $X^-$ is at least one organic or inorganic anion. Suitable anions X⁻ include hydroxide, halide, carboxylate, sulfonate, sulfate, carbonate and bicarbonate.

Where X⁻ is a polyvalent anion such as carbonate or sulfate it is understood that the positive and negative charges in structure III are properly balanced. For example, where $R^3$–$R^6$ in structure III are each methyl groups and X⁻ is carbonate, it is understood that X⁻ represents ½($CO_3^{-2}$).

Quaternary ammonium compounds having structure III and which are suitable for use as phase transfer catalysts according to the method of the present invention are illustrated by methyl tributyl ammonium chloride, tetrabutyl ammonium chloride and decyl trimethyl ammonium chloride.

The amount of phase transfer catalyst employed is in a range between about 0.1 and about 2, preferably between about 0.25 and about 1.0 mole percent catalyst per mole of ester-substituted phenol employed.

In one embodiment of the present invention a tertiary amine is also included as a co-catalyst for the formation of ester-substituted diaryl carbonates. The tertiary amine has been found to accelerate the formation of ester-substituted diary carbonate product and to act to minimize the presence of the intermediate ester-substituted phenyl chloroformate in the product. The optional use of a tertiary amine added after phosgene addition has been completed has been found useful in reaction systems in which the chloroformate intermediates tend to persist. Thus, phosgene addition to a two phase reaction system comprising a water immiscible organic solvent, water, an acid acceptor, an ester-substituted phenol and a phase transfer catalyst under the conditions of the present invention may at times result in the a product mixture comprising ester-substituted diaryl carbonate and the intermediate ester-substituted phenyl chloroformate. Typically, the amount of ester-substituted phenyl chloroformate is low, less than 1 mole percent based upon the total number of moles of phenol employed but its presence in the product is undesirable. It has been found that a small amount of a tertiary amine added following the phosgenation step provides a means of eliminating residual chloroformates, present in the product mixture. Typically, the amount of tertiary amine co-catalyst used is in a range between about 0.01 mole and about 1 mole percent based upon the total number of moles of ester-substituted phenol employed.

Tertiary amines suitable for use as co-catalysts according to the method of the present invention are illustrated by triethylamine, diisopropyl ethyl amine, tributyl amine, and 1,4-diazabicyclooctane.

EXAMPLES

The following examples are set forth to provide those of ordinary skill in the art with a detailed description of how the methods claimed herein are evaluated, and are not intended to limit the scope of what the inventors regard as their invention. Unless indicated otherwise, parts are by weight, temperature is in ° C. In the Tables which follow Examples of the present invention are designated by a number, for example, 1,representing Example 1.Comparative Examples are designated by "CE-number", for example, CE-1 for Comparative Example 1.

Comparative Example 1

A 500 milliliter, 5 neck baffled round bottom flask equipped with a mechanical stirrer, pH probe, sodium hydroxide inlet, condenser, phosgene inlet, nitrogen inlet and gas outlet connected to an efficient phosgene scrubber, was charged with phenol (40.00 g ,0.4255 moles) 112 ml of methylene chloride and 84.5 ml of water. Triethylamine (0.0043 g, 0.0043 moles) was added to the reaction mixture. Phosgene (25.27 g (0.2553 moles) was added at 0.5 grams per minute (g/min) while maintaining a pH of 10.3 with the counter addition of 50% sodium hydroxide. Upon completion of the addition of phosgene, nitrogen was allowed to purge the system for 5 minutes. A sample was taken, quenched with acid and analyzed by liquid chromatography. Phenol was converted in essentially quantitative yield to diphenyl carbonate as determined by HPLC.

Comparative Examples 2–5 were carried out under essentially identical conditions using 20 mole percent excess phosgene except that the pH of the aqueous phase was varied between 10.3 and 7.3. Initial starting concentrations for Comparative Examples 1–5 was 31 percent solids.

TABLE 1

EFFECT OF pH ON ESTER-SUBSTITUTED PHENOL CONVERSION TO DAIRYL CARBONATE

| Example | ArOH | mole % Et₃N | pH | % Conversion |
|---|---|---|---|---|
| CE-1 | phenol | 1 | 10.3 | 100 |
| CE-2 | methyl salicylate | 1 | 10.3 | 73.4 |
| CE-3 | methyl salicylate | 1 | 9.3 | 68.9 |
| CE-4 | methyl salicylate | 1 | 8.3 | 61.4 |
| CE-5 | methyl salicylate | 1 | 7.3 | 44.6 |

The data in Table 1 illustrate that although diphenyl carbonate (Comparative Example 1) may be prepared efficiently using a 20 percent molar excess of phosgene and triethylamine as a catalyst, application of these conditions to methyl salicylate results in incomplete conversion to product bis-methyl salicyl carbonate (BMSC). Conversion of methyl salicylate was incomplete even with the use of 20 percent excess phosgene and showed a strong dependence upon the pH of the aqueous phase.

Example 1

A 500 milliliter, 5-neck baffled round bottom flask equipped with a mechanical stirrer, pH probe, sodium hydroxide inlet, condenser, phosgene inlet, nitrogen inlet and gas outlet connected to an efficient phosgene scrubber, was charged with methyl salicylate (42.92 g, 0.2821 moles), 112 ml of methylene chloride and 84.5 ml of water, and methyl tributyl ammonium chloride (0.0028 mole MTBA). Phosgene (16.76 g, 0.1693 moles) was added at 0.5 grams per minute while maintaining a pH of 10.3 with the counter addition of 50% sodium hydroxide. Upon completion of the phosgene addition, the reaction mixture was purged with nitrogen for 5 minutes. A sample was taken, quenched with acid, and analyzed by liquid chromatography. Methyl salicylate was converted to bis-methyl salicyl carbonate (BMSC) in greater than 99% yield as determined by HPLC.

Data are gathered in Table 2 for Examples 1–7 which illustrate the method of the present invention. Examples 2–7 were carried out essentially identically to Example 1 with the following exceptions. Examples 2–7 each employed a small amount of triethylamine as a co-catatlyst. In Examples 3 and 4 the triethylamine was added prior to phosgenation whereas in Examples 2, 5, 6 and 7 the triethylamine was added after the completion of phosgenation. Examples 1–4 were run at a concentration equivalent to that shown for Comparative Examples 2–5 of Table 1. Starting concentrations for Examples 1–4 and Comparative Examples 1–5 were such that, assuming 100% conversion of methyl salicylate or phenol to product BMSC or DPC, the weight of the product diaryl carbonate would represent 31 percent by weight of the methylene chloride employed at the outset of the reaction. This is designated 31 percent solids. Examples 5, 6 and 7 were run at slightly higher concentrations 37.3, 54.4 and 70 percent solids respectively. At concentrations of about 45 percent solids and higher the product BMSC was observed to precipitate from the reaction mixture and additional methylene chloride was added for work up and HPLC analysis. Examples 1–6 were run at ambient temperature. In Example 7 the reaction mixture was immersed in an ice bath during the reaction. Values for percent conversion of methyl salicylate are provided as well as the selectivity for BMSC. The selectivity is the HPLC peak area generated by the BMSC peak relative to the total peak area of all products peaks present in the crude product sample. In Table 2 the symbol "*" indicates post-phosgenation addition of triethylamine.

TABLE 2

PHASE TRANSFER CATALYSIS OF ESTER-SUBSTITUTED DIARYL CARBONATE FORMATION

| Example | mole % Et$_3$N | mole % PTC | pH | % Conversion | Selectivity |
|---|---|---|---|---|---|
| 1 | 0 | 1 | 10.3 | 100 | 99.8 |
| 2 | 0.05* | 0.5 | 10.3 | 100 | 99.5 |
| 3 | 0.025 | 0.5 | 10.3 | 100 | 99.8 |
| 4 | 0.025 | 0.5 | 10.3 | 100 | 99.3 |
| 5 | 0.5* | 1 | 10.3 | 100 | 99.1 |
| 6 | 0.5* | 1 | 10.3 | 100 | 99.2 |
| 7 | 0.5* | 0.5 | 10.3 | 99.8 | 97.6 |

The data in Table 2 illustrate the high conversions of ester-substituted phenol to ester-substituted carbonate achieved using the method of the present invention.

The invention has been described in detail with particular reference to preferred embodiments thereof, but it will be understood by those skilled in the art that variations and modifications can be effected within the spirit and scope of the invention.

What is claimed is:

1. A method of preparing ester-substituted diaryl carbonates, said method having a contact time, said method comprising contacting an ester-substituted phenol with phosgene and a phase transfer catalyst in the presence of an organic solvent and an aqueous phase wherein the aqueous phase is maintained at a pH of at least about 9.3 throughout the contact time, said phosgene being used in an amount corresponding to between about 0.95 and about 1.20 moles of phosgene per mole of ester-substituted phenol.

2. A method according to claim 1 wherein said ester-substituted diaryl carbonate has structure I

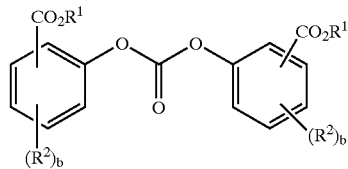

I wherein $R^1$ is independently at each occurrence $C_1$–$C_{20}$ alkyl radical, $C_4$–$C_{20}$ cycloalkyl radical or $C_4$–$C_{20}$ aromatic radical, $R^2$ is independently at each occurrence a hydrogen atom, halogen atom, cyano group, nitro group, $C_1$–$C_{20}$ alkyl radical, $C_4$–$C_{20}$ cycloalkyl radical, $C_4$–$C_{20}$ aromatic radical, $C_1$–$C_{20}$ alkoxy radical, $C_4$–$C_{20}$ cycloalkoxy radical, $C_4$–$C_{20}$ aryloxy radical, $C_1$–$C_{20}$ alkylthio radical, $C_4$–$C_{20}$ cycloalkylthio radical, $C_4$–$C_{20}$ arylthio radical, $C_1$–$C_{20}$ alkylsulfinyl radical, $C_4$–$C_{20}$ cycloalkylsulfinyl radical, $C_4$–$C_{20}$ arylsulfinyl radical, $C_1$–$C_{20}$ alkylsulfonyl radical, $C_4$–$C_{20}$ cycloalkylsulfonyl radical, $C_4$–$C_{20}$ arylsulfonyl radical, $C_1$–$C_{20}$ alkoxycarbonyl radical, $C_4$–$C_{20}$ cycloalkoxycarbonyl radical, $C_4$–$C_{20}$ aryloxycarbonyl radical, $C_2$–$C_{60}$ alkylamino radical, $C_6$–$C_{60}$ cycloalkylamino radical, $C_5$–$C_{60}$ arylamino radical, $C_1$–$C_{40}$ alkylaminocarbonyl radical, $C_4$–$C_{40}$ cycloalkylaminocarbonyl radical, $C_4$–$C_{40}$ arylaminocarbonyl radical, and $C_1$–$C_{20}$ acylamino radical; and b is independently at each occurrence an integer 0–4.

3. A method according to claim 2 wherein the ester-substituted diaryl carbonate is bis-methyl salicyl carbonate.

4. A method according to claim 1 wherein said ester-substituted phenol has structure II

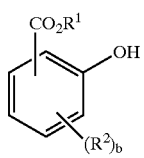

II wherein $R^1$ is $C_1$–$C_{20}$ alkyl radical, $C_4$–$C_{20}$ cycloalkyl radical or $C_4$–$C_{20}$ aromatic radical, $R^2$ is independently at each occurrence a hydrogen atom, halogen atom, cyano group, nitro group, $C_1$–$C_{20}$ alkyl radical, $C_4$–$C_{20}$ cycloalkyl radical, $C_4$–$C_{20}$ aromatic radical, $C_1$–$C_{20}$ alkoxy radical, $C_4$–$C_{20}$ cycloalkoxy radical, $C_4$–$C_{20}$ aryloxy radical, $C_1$–$C_{20}$ alkylthio radical, $C_4$–$C_{20}$ cycloalkylthio radical, $C_4$–$C_{20}$ arylthio radical, $C_1$–$C_{20}$ alkylsulfinyl radical, $C_4$–$C_{20}$ cycloalkylsulfinyl radical, $C_4$–$C_{20}$ arylsulfinyl radical, $C_1$–$C_{20}$ alkylsulfonyl radical, $C_4$–$C_{20}$ cycloalkylsulfonyl radical, $C_4$–$C_{20}$ arylsulfonyl radical, $C_1$–$C_{20}$ alkoxycarbonyl radical, $C_4$–$C_{20}$ cycloalkoxycarbonyl radical, $C_4$–$C_{20}$ aryloxycarbonyl radical, $C_2$–$C_{60}$ alkylamino radical, $C_6$–$C_{60}$ cycloalkylamino radical, $C_5$–$C_{60}$ arylamino radical, $C_1$–$C_{40}$ alkylaminocarbonyl radical, $C_4$–$C_{40}$ cycloalkylaminocarbonyl radical, $C_4$–$C_{40}$ arylaminocarbonyl radical, and $C_1$–$C_{20}$ acylamino radical; and b is an integer 0–4.

5. A method according to claim 4 wherein said ester-substituted phenol is selected from the group consisting of methyl salicylate, ethyl salicylate, isopropyl salicylate and benzyl salicylate.

6. A method according to claim 1 wherein said phase transfer catalyst comprises a quaternary ammonium compound having structure III

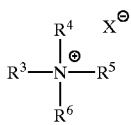

III wherein $R^3$–$R^6$ are independently a $C_1$–$C_{20}$ alkyl radical, $C_4$–$C_{20}$ cycloalkyl radical or a $C_4$–$C_{20}$ aryl radical and $X^-$ is at least one organic or inorganic anion. Suitable anions $X^-$ include hydroxide, halide, carboxylate, sulfonate, sulfate, carbonate and bicarbonate.

7. A method according to claim 6 wherein said phase transfer catalyst is selected from the group consisting of methyl tributyl ammonium chloride, tetrabutyl ammonium chloride and decyl trimethyl ammonium chloride.

8. A method according to claim 1 wherein said aqueous phase is maintained at a pH in a range between about 9.3 and about 12.

9. A method according to claim 8 wherein said aqueous phase is maintained at a pH in a range between about 9.3 and about 12 by the addition of aqueous alkali metal hydroxide, aqueous alkaline earth metal hydroxide, or a mixture thereof.

10. A method according to claim 9 wherein the alkali metal hydroxide is sodium hydroxide.

11. A method according to claim 1 wherein said solvent is a halogenated solvent.

12. A method according to claim 11 wherein said halogenated solvent is methylene chloride.

13. A method according to claim 1 wherein said solvent is a non-halogenated solvent.

14. A method according to claim 13 wherein said solvent is toluene.

15. A method according to claim 1 wherein the phase transfer catalyst is present in a range between about 0.1 and about 2 mole percent based upon the number of moles of ester-substituted phenol.

16. A method of preparing ester-substituted diaryl carbonates, said method having a contact time, said method comprising contacting an ester-substituted phenol with phosgene, a phase transfer catalyst, and a tertiary amine, in the presence of an organic solvent and an aqueous phase wherein the aqueous phase is maintained at a pH of at least about 9.3 throughout the contact time, said phosgene being used in an amount corresponding to between about 0.95 and about 1.10 molar equivalents based on said ester-substituted phenol, whereby at least 90% of the ester-substituted phenol is converted into product ester-substituted diaryl carbonate.

17. A method according to claim 16 wherein said phase transfer catalyst comprises a quaternary ammonium compound having structure III

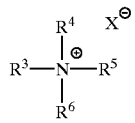

III wherein $R^3$–$R^6$ are independently a $C_1$–$C_{20}$ alkyl radical, $C_4$–$C_{20}$ cycloalkyl radical or a $C_4$–$C_{20}$ aryl radical and $X^-$ is at least one organic or inorganic anion. Suitable anions $X^-$ include hydroxide, halide, carboxylate, sullfonate, sulfate, carbonate and bicarbonate.

18. A method according to claim 1 wherein the tertiary amine is selected from the group consisting of triethylamine, diispropyl ethyl amine, tributyl amine, and 1,4-diazabicyclooctane.

19. A method according to claim 18 wherein the amine is triethylamine.

20. A method of preparing bis-methyl salicyl carbonate said method comprising contacting a two phase mixture of a solution of methyl salicylate in methylene chloride and an aqueous phase, with from about 0.95 to about 1.10 molar equivalents of phosgene and from about 0.1 to about 2 molar equivalents of a quaternary ammonium compound, said molar equivalents of phosgene and quaternary ammonium compound being based on the number of moles of methyl salicylate employed, said aqueous phase being maintained at a pH of between about 9.3 and about 12 by the addition of aqueous sodium hydroxide solution, whereby at least 90% of the methyl salicylate is converted into product bis-methyl salicyl carbonate.

21. A method according to claim 20 wherein said quaternary ammonium compound has structure III

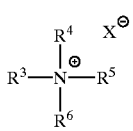

III wherein $R^3$–$R^6$ are independently a $C_1$–$C_{20}$ cycloalkyl radical, $C_4$–$C_{20}$ cycloalkyl radical or a $C_4$–$C_{20}$ aryl radical and $X^-$ is at least one organic or inorganic anion. Suitable anions $X^-$ include hydroxide, halide, carboxylate, sullfonate, sulfate, carbonate and bicarbonate.

22. A method according to claim 21 wherein structure III is methyl tributyl ammonium chloride.

* * * * *